US009901388B2

(12) United States Patent
Batchelor et al.

(10) Patent No.: US 9,901,388 B2
(45) Date of Patent: Feb. 27, 2018

(54) HAND SWITCHED COMBINED ELECTROSURGICAL MONOPOLAR AND BIPOLAR DEVICE

(71) Applicant: GYRUS ACMI, INC., Southborough, MA (US)

(72) Inventors: Kester J. Batchelor, Mound, MN (US); Richard Curtis, Maple Grove, MN (US); Jyue Boon (Jonas) Lim, New Brighton, MN (US); Tsuyoshi Hayashida, Maple Grove, MN (US); John Mensch, Plymouth, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 278 days.

(21) Appl. No.: 14/209,071

(22) Filed: Mar. 13, 2014

(65) Prior Publication Data

US 2014/0276798 A1    Sep. 18, 2014

Related U.S. Application Data

(60) Provisional application No. 61/787,731, filed on Mar. 15, 2013.

(51) Int. Cl.
*A61B 18/14* (2006.01)
*A61B 18/12* (2006.01)
*A61B 18/00* (2006.01)

(52) U.S. Cl.
CPC .......... *A61B 18/14* (2013.01); *A61B 18/1233* (2013.01); *A61B 18/1442* (2013.01); *A61B 2018/00178* (2013.01); *A61B 2018/00601* (2013.01); *A61B 2018/00916* (2013.01); *A61B 2018/00922* (2013.01); *A61B 2018/00928* (2013.01); *A61B 2018/00958* (2013.01);
(Continued)

(58) Field of Classification Search
CPC ........... A61B 2018/00172; A61B 2018/00178; A61B 2018/00916; A61B 2018/00922; A61B 2018/00946
See application file for complete search history.

(56) References Cited

U.S. PATENT DOCUMENTS 1,198,958 A   9/1916  Risely
2,042,985 A   6/1936  Gardella
(Continued)

FOREIGN PATENT DOCUMENTS

CN   1149519 A    5/1997
CN   102164556    8/2011
(Continued)

OTHER PUBLICATIONS

International Search Report and Written Opinion for Application No. PCT/US2014/025999 dated Jul. 22, 2014.
(Continued)

*Primary Examiner* — Ronald Hupczey, Jr.
*Assistant Examiner* — Bo Ouyang
(74) *Attorney, Agent, or Firm* — The Dobrusin Law Firm, PC

(57) ABSTRACT

An electrosurgical instrument connectivity system providing monopolar and bipolar plugs each having a plurality of conductors which allow for use of combination monopolar/bipolar electrosurgical devices with industry standard electrosurgical generator outlets.

12 Claims, 5 Drawing Sheets

(52) U.S. Cl.
CPC ............. *A61B 2018/1412* (2013.01); *A61B 2018/1462* (2013.01)

(56) References Cited

U.S. PATENT DOCUMENTS

| | | | |
|---|---|---|---|
| 2,214,984 A | 9/1940 | Bachmann | |
| 2,381,084 A | 8/1945 | Slad | |
| 2,575,652 A | 11/1951 | Bovee | |
| 2,894,424 A | 7/1959 | Vaughan | |
| 3,399,583 A | 9/1968 | Hall | |
| 3,417,752 A | 12/1968 | Butler | |
| 3,465,621 A | 9/1969 | Ladd | |
| 3,576,072 A | 4/1971 | Foster | |
| 3,643,663 A | 2/1972 | Sutter | |
| 3,685,518 A | 8/1972 | Beuerle et al. | |
| 3,699,632 A | 10/1972 | Anhalt | |
| 3,818,784 A | 6/1974 | McClure | |
| 3,913,586 A | 10/1975 | Baumgarten | |
| 4,041,952 A | 8/1977 | Morrison, Jr. et al. | |
| 4,154,226 A | 5/1979 | Hennig et al. | |
| 4,171,700 A * | 10/1979 | Farin .................. | A61B 18/1233 606/34 |
| 4,202,337 A | 5/1980 | Hren et al. | |
| 4,318,313 A | 3/1982 | Tartaglia | |
| 4,375,218 A | 3/1983 | DiGeronimo | |
| 4,407,069 A | 10/1983 | Conners | |
| 4,418,692 A | 12/1983 | Guay | |
| 4,443,935 A | 4/1984 | Zamba et al. | |
| 4,463,759 A | 8/1984 | Garito et al. | |
| 4,492,231 A | 1/1985 | Auth | |
| 4,492,832 A | 1/1985 | Taylor | |
| 4,494,543 A | 1/1985 | Hart | |
| 4,504,707 A | 3/1985 | Ochiai | |
| 4,524,648 A | 6/1985 | Chung | |
| 4,552,143 A | 11/1985 | Lottick | |
| 4,655,215 A | 4/1987 | Pike | |
| 4,669,470 A | 6/1987 | Brandfield | |
| 4,686,980 A | 8/1987 | Williams et al. | |
| 4,713,885 A | 12/1987 | Keklak et al. | |
| 4,757,612 A | 7/1988 | Peyrot | |
| 4,784,136 A | 11/1988 | Klein | |
| 4,860,745 A | 8/1989 | Farin et al. | |
| 4,896,661 A | 1/1990 | Bogert et al. | |
| 4,935,027 A | 6/1990 | Yoon | |
| 5,021,616 A | 6/1991 | Hardt | |
| 5,035,695 A | 7/1991 | Weber, Jr. et al. | |
| 5,071,426 A | 12/1991 | Dolgin et al. | |
| 5,104,397 A | 4/1992 | Vasconcelos et al. | |
| 5,108,392 A | 4/1992 | Spingler | |
| 5,147,378 A | 9/1992 | Markham | |
| 5,176,702 A | 1/1993 | Bales et al. | |
| 5,190,541 A | 3/1993 | Abele et al. | |
| 5,196,009 A | 3/1993 | Kirwan, Jr. | |
| 5,207,691 A | 5/1993 | Nardella | |
| 5,207,696 A | 5/1993 | Matwijcow | |
| 5,208,983 A | 5/1993 | Masse | |
| 5,226,904 A | 7/1993 | Gentelia et al. | |
| 5,281,216 A | 1/1994 | Klicek | |
| 5,290,286 A | 3/1994 | Parins | |
| 5,293,878 A | 3/1994 | Bales et al. | |
| 5,318,589 A | 6/1994 | Lichtman | |
| 5,342,359 A | 8/1994 | Rydell | |
| 5,370,659 A | 12/1994 | Sakashita | |
| 5,403,312 A | 4/1995 | Yates et al. | |
| 5,413,575 A | 5/1995 | Haenggi | |
| 5,423,814 A | 6/1995 | Zhu et al. | |
| 5,425,743 A | 6/1995 | Nicholas | |
| 5,440,813 A | 8/1995 | Roskam | |
| 5,441,498 A | 8/1995 | Perkins | |
| 5,443,463 A | 8/1995 | Stern et al. | |
| 5,456,695 A | 10/1995 | Herve Dallemagne | |
| 5,458,598 A | 10/1995 | Feinberg et al. | |
| 5,472,442 A | 12/1995 | Klicek | |
| 5,483,952 A | 1/1996 | Aranyi | |
| 5,484,435 A * | 1/1996 | Fleenor .............. | A61B 18/1442 606/46 |
| 5,499,998 A | 3/1996 | Meade | |
| 5,531,744 A | 7/1996 | Nardella et al. | |
| 5,540,685 A | 7/1996 | Parins et al. | |
| 5,562,503 A | 10/1996 | Ellman et al. | |
| 5,573,424 A | 11/1996 | Poppe | |
| 5,626,577 A | 5/1997 | Harris | |
| 5,658,281 A | 8/1997 | Heard | |
| 5,693,052 A | 12/1997 | Weaver | |
| 5,702,390 A | 12/1997 | Austin et al. | |
| 5,709,680 A | 1/1998 | Yates et al. | |
| 5,735,849 A | 4/1998 | Baden et al. | |
| 5,779,701 A | 7/1998 | McBrayer et al. | |
| 5,810,805 A | 9/1998 | Sutcu et al. | |
| 5,827,281 A | 10/1998 | Levin | |
| 5,884,954 A | 3/1999 | Trozera | |
| 5,891,140 A | 4/1999 | Ginn et al. | |
| 5,902,301 A | 5/1999 | Olig | |
| 5,922,001 A | 7/1999 | Yoon | |
| 5,951,545 A | 9/1999 | Schilling et al. | |
| 6,024,741 A | 2/2000 | Williamson, IV et al. | |
| 6,030,384 A | 2/2000 | Nezhat | |
| 6,039,734 A | 3/2000 | Goble | |
| 6,050,996 A | 4/2000 | Schmaltz et al. | |
| 6,053,908 A | 4/2000 | Crainich et al. | |
| 6,074,386 A | 6/2000 | Goble et al. | |
| 6,102,909 A | 8/2000 | Chen et al. | |
| 6,110,171 A | 8/2000 | Rydell | |
| 6,113,596 A * | 9/2000 | Hooven .............. | A61B 18/14 606/42 |
| 6,117,158 A | 9/2000 | Measamer et al. | |
| 6,117,169 A | 9/2000 | Moe | |
| 6,152,923 A | 11/2000 | Ryan | |
| 6,190,386 B1 | 2/2001 | Rydell | |
| 6,270,497 B1 | 8/2001 | Sekino et al. | |
| 6,273,887 B1 | 8/2001 | Yamauchi et al. | |
| 6,325,795 B1 | 12/2001 | Lindemann et al. | |
| 6,355,032 B1 | 3/2002 | Hovda et al. | |
| 6,358,268 B1 | 3/2002 | Hunt et al. | |
| 6,402,747 B1 | 6/2002 | Lindemann et al. | |
| 6,428,538 B1 | 8/2002 | Blewett et al. | |
| 6,458,128 B1 | 10/2002 | Schulze | |
| 6,464,704 B2 | 10/2002 | Schmaltz et al. | |
| 6,486,419 B2 | 11/2002 | Horiguchi et al. | |
| 6,494,886 B1 | 12/2002 | Wilk et al. | |
| 6,514,252 B2 | 2/2003 | Nezhat et al. | |
| 6,551,313 B1 | 4/2003 | Levin | |
| 6,585,735 B1 | 7/2003 | Frazier et al. | |
| 6,619,038 B2 | 9/2003 | Takada et al. | |
| 6,623,499 B1 | 9/2003 | Andreini et al. | |
| 6,641,595 B1 | 11/2003 | Moran et al. | |
| 6,652,514 B2 | 11/2003 | Ellman et al. | |
| 6,679,882 B1 | 1/2004 | Kornerup | |
| 6,689,130 B2 | 2/2004 | Arai et al. | |
| 6,695,840 B2 | 2/2004 | Schulze | |
| 6,726,686 B2 | 4/2004 | Buysse et al. | |
| 6,749,610 B2 | 6/2004 | Kirwan, Jr. et al. | |
| 6,752,767 B2 | 6/2004 | Turovskiy et al. | |
| 6,773,434 B2 | 8/2004 | Ciarrocca | |
| 6,808,525 B2 | 10/2004 | Latterell et al. | |
| 6,827,717 B2 | 12/2004 | Brommersma et al. | |
| 6,860,882 B2 | 3/2005 | Battles et al. | |
| 6,926,716 B2 | 8/2005 | Baker et al. | |
| 6,942,662 B2 | 9/2005 | Goble et al. | |
| 7,083,613 B2 | 8/2006 | Treat | |
| 7,094,231 B1 | 8/2006 | Ellman et al. | |
| 7,108,694 B2 | 9/2006 | Miura et al. | |
| 7,112,199 B2 | 9/2006 | Cosmescu | |
| 7,147,637 B2 | 12/2006 | Goble | |
| 7,150,749 B2 | 12/2006 | Dycus et al. | |
| 7,156,846 B2 | 1/2007 | Dycus et al. | |
| 7,232,440 B2 | 6/2007 | Dumbauld et al. | |
| 7,244,257 B2 | 7/2007 | Podhajsky et al. | |
| 7,252,667 B2 | 8/2007 | Moses et al. | |
| 7,344,536 B1 | 3/2008 | Lunsford et al. | |
| 7,367,976 B2 | 5/2008 | Lawes et al. | |
| 7,377,902 B2 | 5/2008 | Burbank | |
| 7,481,810 B2 | 1/2009 | Dumbauld et al. | |
| 7,503,917 B2 | 3/2009 | Sartor et al. | |
| 7,604,635 B2 | 10/2009 | McClurken et al. | |

(56) References Cited

U.S. PATENT DOCUMENTS

| | | | |
|---|---|---|---|
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 * | 4/2014 | Weber ............... A61B 18/14 606/34 |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shilev et al. |
| 9,358,065 B2 | 6/2016 | Ladtkow et al. |
| 9,439,665 B2 | 9/2016 | Marczyk et al. |
| 9,452,011 B2 | 9/2016 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2003/0018329 A1 | 1/2003 | Hooven |
| 2003/0050633 A1 | 3/2003 | Ellman |
| 2003/0097126 A1 | 5/2003 | Woloszko |
| 2003/0109876 A1 | 6/2003 | Yamauchi |
| 2003/0114850 A1 | 6/2003 | McClurken |
| 2003/0144652 A1 | 7/2003 | Baker et al. |
| 2003/0181904 A1 | 9/2003 | Levine et al. |
| 2004/0030330 A1 | 2/2004 | Brassell et al. |
| 2004/0082946 A1 | 4/2004 | Malis |
| 2004/0097117 A1 | 5/2004 | Gonnering |
| 2005/0065510 A1 | 3/2005 | Carmel et al. |
| 2005/0113824 A1 | 5/2005 | Sartor |
| 2005/0113825 A1 | 5/2005 | Cosmescu |
| 2005/0113827 A1 | 5/2005 | Dumbauld et al. |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0084973 A1 | 4/2006 | Hushka |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dumbauld et al. |
| 2007/0093857 A1 | 4/2007 | Rogers et al. |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0093804 A1 | 4/2009 | Newton |
| 2009/0138003 A1 | 5/2009 | Deville et al. |
| 2009/0138013 A1 | 5/2009 | Thorne et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller |
| 2011/0054462 A1 * | 3/2011 | Ellman ............... A61B 18/1206 606/33 |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0319892 A1 | 12/2011 | Blomeyer |
| 2012/0022530 A1 | 1/2012 | Woodruff |
| 2012/0078292 A1 | 3/2012 | Banju |
| 2012/0095460 A1 | 4/2012 | Rooks et al. |
| 2012/0101501 A1 | 4/2012 | Nishimura et al. |
| 2012/0123405 A1 | 5/2012 | Moua et al. |
| 2012/0150165 A1 | 6/2012 | Conley |
| 2012/0202388 A1 | 8/2012 | Selig |
| 2013/0023874 A1 | 1/2013 | Lawes |
| 2013/0066317 A1 | 3/2013 | Evans et al. |
| 2013/0079762 A1 | 3/2013 | Twomey et al. |
| 2013/0178852 A1 * | 7/2013 | Allen, IV ............ A61B 18/1442 606/42 |
| 2013/0237982 A1 | 9/2013 | Rencher et al. |
| 2013/0296846 A1 | 11/2013 | Canady et al. |
| 2014/0100569 A1 | 4/2014 | Lawes et al. |
| 2014/0236202 A1 | 8/2014 | Palmer et al. |
| 2014/0276772 A1 | 9/2014 | Batchelor et al. |
| 2014/0276785 A1 | 9/2014 | Batchelor et al. |
| 2014/0276786 A1 | 9/2014 | Batchelor |
| 2014/0276794 A1 | 9/2014 | Batchelor et al. |
| 2014/0276795 A1 | 9/2014 | Batchelor et al. |
| 2014/0276796 A1 | 9/2014 | Batchelor et al. |
| 2014/0276797 A1 | 9/2014 | Batchelor et al. |
| 2014/0276798 A1 | 9/2014 | Batchelor et al. |
| 2014/0276799 A1 | 9/2014 | Batchelor et al. |
| 2014/0276800 A1 | 9/2014 | Batchelor et al. |
| 2014/0276804 A1 | 9/2014 | Batchelor |
| 2015/0119885 A1 | 4/2015 | Windgassen et al. |
| 2015/0148798 A1 | 5/2015 | Windgassen et al. |
| 2015/0320485 A1 | 11/2015 | Batchelor et al. |

FOREIGN PATENT DOCUMENTS

| | | |
|---|---|---|
| CN | 102836006 | 12/2012 |
| EP | 0392548 A1 | 10/1994 |
| EP | 1089664 | 4/2001 |
| EP | 1530952 | 5/2005 |
| EP | 1530952 A1 | 5/2005 |
| EP | 1769765 A1 | 4/2007 |
| EP | 1810629 | 7/2007 |
| EP | 1810629 A2 | 7/2007 |
| EP | 1977706 | 10/2008 |
| EP | 1977706 A1 | 10/2008 |
| EP | 2403422 | 1/2012 |
| JP | H10-137259 A | 5/1998 |
| JP | H10-504485 A | 5/1998 |
| JP | 2000070280 A | 3/2000 |
| JP | 2001170070 A | 6/2001 |
| JP | 2004508875 A | 3/2004 |
| JP | 2005144192 A | 6/2005 |
| JP | 2005521465 A | 7/2005 |
| JP | 2009247893 A | 10/2009 |

(56) References Cited

FOREIGN PATENT DOCUMENTS

| | | | |
|---|---|---|---|
| JP | 2012518490 A | 8/2012 | |
| WO | 96/05776 A1 | 2/1996 | |
| WO | 9966850 | 12/1999 | |
| WO | 02/24089 A1 | 3/2002 | |
| WO | 2006/122279 | 11/2006 | |
| WO | 2007/002545 | 1/2007 | |
| WO | 2007/093857 | 8/2007 | |
| WO | 2010/101897 | 9/2010 | |
| WO | 2012/053530 A | 4/2012 | |
| WO | 2014/096815 A2 | 6/2014 | |

OTHER PUBLICATIONS

Potentially related U.S. Appl. No. 14/177,780, filed Feb. 11, 2014.
Potentially related U.S. Appl. No. 14/178,411, filed Feb. 12, 2014.
Potentially related U.S. Appl. No. 14/205,598, filed Mar. 12, 2014.
Potentially related U.S. Appl. No. 14/205,919, filed Mar. 12, 2014.
Potentially related to U.S. Appl. No. 14/206,010, filed Mar. 12, 2014.
Potentially related U.S. Appl. No. 14/210,535, filed Mar. 14, 2014.
Potentially related U.S. Appl. No. 14/210,741, filed Mar. 14, 2014.
Potentially related U.S. Appl. No. 14/211,042, filed Mar. 14, 2014.
Potentially related U.S. Appl. No. 14/178,569, filed Feb. 12, 2014.
Potentially related U.S. Appl. No. 14/178,577, filed Feb. 12, 2014.
315MHZ sliding remote cover, available at website: http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).
Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).
Potentially related U.S. Appl. No. 14/829,725, filed Aug. 19, 2015.
Potentially related U.S. Appl. No. 14/830,069, filed Aug. 19, 2015.
Potentially related U.S. Appl. No. 14/830,255, filed Aug. 19, 2015.
PCT International Preliminary Report on Patentability dated Sep. 24, 2015 for Application No. PCT/US2014/025999.
Japanese Office Action dated Nov. 1, 2016 for Application No. 2016-502020.
Chinese Office Action dated Dec. 2, 2016 for Application No. 201480015301.X.
European Patent Office Action dated Dec. 13, 2016 for Application No. 14720793.0.

* cited by examiner

HAND SWITCHED COMBINED ELECTROSURGICAL MONOPOLAR AND BIPOLAR DEVICE

FIELD

The present teachings generally relate to electrosurgical instrument connector configurations and devices for use in combination monopolar/bipolar electrosurgical devices. More specifically, the present teachings allow for the use of combination monopolar/bipolar electrosurgical devices using industry standard connectors (e.g., plugs).

BACKGROUND

Typically, industry standard electrosurgical generators can be utilized with stand-alone monopolar and stand-alone bipolar electrosurgical devices. However, it is often desired that a surgeon have the capability of switching between monopolar and bipolar devices during surgical procedures. Such switching may cause delays which result in additional challenges during surgical procedures. The development of combination monopolar/bipolar electrosurgical instruments has allowed for simplified switching between monopolar and bipolar functionality during surgical procedures. However, such combination devices generally require a dedicated outlet (e.g., port) in the electrosurgical generator and as such, cannot be utilized with industry standard generators. Thus, the use of such combination devices typically requires a generator having a dedicated output port for dual functionality.

Some examples of such combination devices and associated connectors may be found in U.S. Pat. Nos. 4,463,759; 6,113,596; 6,652,514; 7,232,440; 7,722,607, and U.S. Publication Nos. 2011/0054462; and 2011/0178515, all of which are incorporated by reference herein for all purposes. It would be desirable to have an electrosurgical device connector system which would allow for the use of combination monopolar/bipolar devices with industry standard electrosurgical generators. It would be further beneficial to have combination monopolar/bipolar electrosurgical devices that can be used without a dedicated outlet in an electrosurgical generator.

SUMMARY

The present teachings meet one or more of the needs identified herein by providing a connectivity system including an electric cable for use with an electrosurgical instrument comprising a first plug including a first, second and third conductor extending therefrom, wherein the first and second conductors are first and second electrosurgical leads and the third conductor is a first electrosurgical activation switch return lead. The system may further include a first electrosurgical activation switch connected between one of the electrosurgical leads and the first electrosurgical activation switch return lead. The system may also include a second plug including a fourth, fifth and optionally a sixth conductor extending therefrom, wherein the fourth conductor is a third electrosurgical lead and the fifth and sixth conductors are second and third electrosurgical activation switch return leads. A second electrosurgical activation switch may also be included whereby the second activation switch is connected between the fourth conductor and the fifth conductor. The system may further include a third electrosurgical activation switch connected between the fourth conductor and the sixth conductor. The system may be designed such that the third conductor is common with one of the fifth or sixth conductors.

In another embodiment of the present teachings, the system may comprise a first plug configured to plug into a bipolar outlet, the first plug including three conductors extending therefrom wherein a first and second conductor are bipolar HF (high frequency electric current) leads, and a third conductor is a bipolar switch return lead. The system may further comprise a bipolar activation switch connecting one of the bipolar HF leads and the bipolar switch return lead and a second plug configured to plug into a monopolar outlet, the second plug including two conductors extending therefrom wherein a fourth conductor is a monopolar HF lead and a fifth conductor is a monopolar switch return lead. The system may also include a monopolar activation switch connecting the monopolar HF lead and the monopolar switch return lead. The system may be provided so that the bipolar switch return lead is common with one of the monopolar switch return leads, so that four or less conductors are used.

Another possible embodiment of the present teachings includes a cable comprising a first plug configured to plug into a bipolar outlet, the first plug including a first, second and third bipolar conductor extending therefrom, wherein the first and second bipolar conductors are bipolar HF leads and the third bipolar conductor is a bipolar switch return lead. The cable may further comprise a bipolar activation switch connected between one of the bipolar HF leads and the bipolar switch return lead. The cable may also include a second plug adapted to plug into a monopolar outlet, the second plug including a first, second and third monopolar conductor extending therefrom, wherein the first monopolar conductor is a monopolar HF lead and the second and third monopolar conductors are monopolar switch return leads. The cable may further include a monopolar cut activation switch connected between the monopolar HF lead and the second monopolar switch return lead and a monopolar coag activation switch connected between the monopolar HF lead and the third monopolar switch return lead. The cable may be constructed so that the bipolar switch return, lead also operates as one of the second or third monopolar switch return leads.

The teachings herein provide for electrosurgical instrument connectivity systems and cables that facilitate the use of combination monopolar/bipolar electrosurgical devices with industry standard electrosurgical generators and avoid the need for proprietary and/or devoted outlets for such devices.

DETAILED DESCRIPTION

Figure 1:
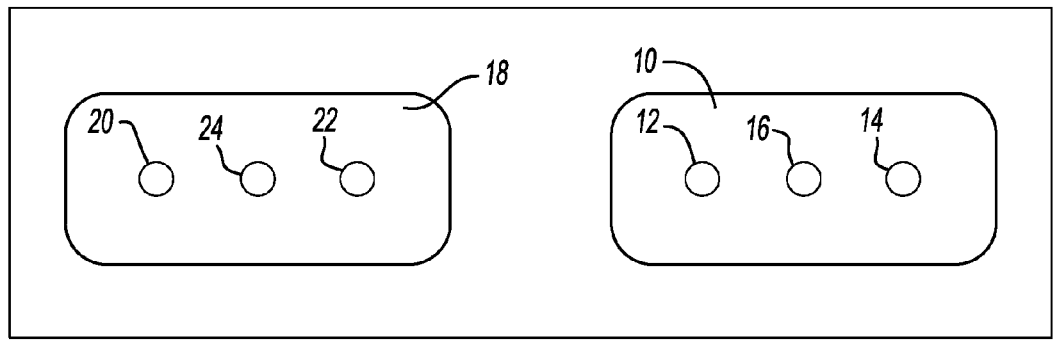
FIG. 1 shows example of traditional monopolar and bipolar outlets of an electrosurgical generator.

This application is related to and claims the benefit of the filing date of U.S. Provisional Application Ser. No. 61/787,731 filed Mar. 15, 2013, the contents of this application being hereby incorporated by reference for all purposes.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings are directed toward electrosurgical instrument connectivity systems. Such systems are generally those associated with electrosurgical forceps and more specifically, with combination monopolar/bipolar electrosurgical forceps. The electrosurgical instruments which are associated with the connectivity systems may be any device that is used by a surgeon to perform a surgical procedure. The electrosurgical device may be used to cut, perform hemostasis, coagulate, desiccate, fulgurate, electrocauterize, or any combination thereof. The electrosurgical instrument connectivity systems disclosed herein are preferably utilized with industry standard outlets associated with electrosurgical generators as opposed to generator outlets devoted specifically to combination monopolar/bipolar devices. The connectivity systems described herein are preferably utilized in either open or laparoscopic surgery as opposed to solely laparoscopic procedures.

As mentioned above, the connectivity systems are preferably utilized with combination monopolar/bipolar devices. The connectivity systems may be designed so that one or more conductors associated with either a monopolar or bipolar plug are integrated with other conductors to form common conductors that provide the functionality of both of the integrated conductors. Typically, industry standard electrosurgical generators include a monopolar plug and a bipolar plug, each connecting to one or more ports (e.g., outlets) (e.g., one, two or three or more bipolar ports, and one, two, three or more monopolar ports). Preferably, each connector (e.g., plug) includes leads connecting to one or more outlets. In most standard generators, at least one of the bipolar outlets and at least one of the monopolar outlets may be an HF outlet for connecting to an HF lead and transmitting electrical current. Preferably, the bipolar plug connects to two HF outlets and the monopolar plug connects to only one HF outlet. Any remaining connectors may be electrosurgical switch return leads. For example, the monopolar plug may include one or more monopolar switch return leads and the bipolar plug may include one or more bipolar switch return leads. Each such switch return lead may be a cut switch return lead or a coag switch return lead. In one preferred embodiment, the bipolar plug may include one switch return lead and the monopolar plug may include two switch return leads.

The monopolar and bipolar HF leads may remain isolated (e.g., each plug may extend from the generator to a device free of commonality with other HF or switch leads). Alternatively, one or more HF leads may be joined with another HF lead, thus minimizing the lines and complexity of cables required for connectivity. As one example, a bipolar HF lead may share a common line with a monopolar HF lead.

The connectivity may also be modified so that the monopolar conductors provide only one of cut or coag functionality. As a result, the connectivity would allow for one monopolar switch and one bipolar switch (as opposed to one bipolar switch and two monopolar switches). Thus, the monopolar functionality (either cut or coag) would be predetermined on the switch line selected. This arrangement may be utilized with either the isolated HF leads or with the joined (e.g., common) HF leads as discussed above. As another example, the connectivity system may be arranged so that the bipolar switch lead is common with one of the monopolar switch leads (e.g., the monopolar cut switch lead or the monopolar coag switch lead). This arrangement would rely on the switch leads that are not active to provide isolation between HF lines (e.g., when bipolar coag is pressed, the monopolar coag switch isolates the two bipolar HF lines).

The connectivity system may be arranged so that there is no common line sharing. Thus, the connectivity system may include a first connector and a second connector. The first connector may be a bipolar plug and the second connector may be a monopolar plug. The first and second connectors may each include one or more conductors. They may each include two or more conductors. They may each include three or more conductors. Each of the first and second connector may have the same number of conductors or may have differing numbers of conductors. Each of the conductors may be HF leads or switch return leads. Each connector may have multiple HF leads and only one switch return lead, or each connector may have multiple switch return leads and only one HF lead. The bipolar plug may include one or more bipolar HF leads. The bipolar plug may include one or more bipolar switch return leads. The bipolar plug may include two bipolar HF leads and one bipolar switch return leads (e.g., two conductors are bipolar HF leads and one conductor is a bipolar switch return lead). The bipolar plug may include exactly one bipolar switch return lead. The monopolar plug may include one or more monopolar HF leads. The monopolar plug may include one or more monopolar switch return leads. The monopolar plug may include one monopolar HF lead. The monopolar plug may include two monopolar switch return leads (e.g., two conductors are monopolar switch return leads and one conductor is a monopolar HF lead). The monopolar plug may include exactly one monopolar HF lead. Each of the monopolar switch return leads may be selected from monopolar cut switch return leads or monopolar coag switch return leads. The connectivity system may include only one monopolar switch return lead, which may be one of a cut switch return lead or coag switch return lead. Thus the functionality of the electrosurgical device may be reduced in that only cut or only coag capability may be present in monopolar mode.

As an alternative to connectivity systems where there is no common line sharing, one or more of the conductors discussed above may have a shared connectivity lines with other conductors to reduce the cable complexity. In other words, one or more HF leads may share a line (e.g., may be integrated) with one or more other HF leads or one or more switch return leads. More specifically, one of the bipolar HF leads may be common with one or the monopolar HF leads. In the event that there are two bipolar HF leads and one monopolar HF lead, the monopolar HF lead may be common with either one of the bipolar HF leads. Such an arrangement may be combined with any other arrangements suggested herein. For example, one or more HF leads may share a common line while the monopolar plug includes only one switch return lead, thereby reducing the number of lines utilized by two. In another embodiment, one or more switch return leads may share a common line. As one specific example, a bipolar switch return lead may be common with a monopolar switch return lead. In an embodiment where there are two monopolar switch return leads (one cut, one coag), the bipolar switch return lead may be common with either of the monopolar switch return leads. Such an arrangement would reduce the number of lines by one and may be combined with other arrangements discussed herein to reduce the number of lines by two. Even more specifically, one or more HF leads may be common and one or more switch return leads while only monopolar functionality is present (cut only or coag only). As a result, the number of lines may be reduced by three.

The electrosurgical devices for which the connectivity systems described herein may be applicable include electrosurgical forceps. Accordingly, the connectivity systems may include one or more activation switches. Each activation is located such that the mode in which the forceps are functioning can be alternated via the activation switches. For example, the device may include one or more bipolar activation switches and one or more monopolar activation switches. More specifically, the monopolar activation switches may comprise a monopolar cut activation switch and a monopolar coag activation switch.

Typically, electrosurgical forceps are stand-alone monopolar or stand-alone bipolar devices which connect to an electrosurgical generator as shown at FIG. 1. Combination monopolar/bipolar forceps typically connect to an electrosurgical generator via a dedicated outlet (as opposed to the outlets shown at FIG. 1). The connectivity systems shown at FIGS. 2-9 however, allow for combination monopolar/bipolar forceps to function using the standard outlets shown at FIG. 1. The forceps may be any forceps that may be used to grip, hold, squeeze, or a combination thereof one or more objects. The forceps may include one or more finger grips (i.e., configured like scissors) that may be used to move the forceps so that they may be used to grip one or more objects. The forceps may be free of finger grips and be actuated by direct pressure being applied to opposing sides of the forceps so that the forceps close and grip an object. The forceps include the first and second arms.

The arms of the forceps may be located within a housing. The housing may be any device that may include one or more arms and be gripped by a user during use. The housing may provide for electrical connection, mechanical connection or a combination thereof between two or more arms. The housing includes space to facilitate connection of the forceps to an electrosurgical generator via one or more cables (e.g., one or more wires housed within one or more cables). Thus one or more cables may extend from the housing at one or more locations along the housing. The housing may be electrically insulating. The housing may include one or more activation buttons. The activation buttons may allow for switching between monopolar and bipolar mode during use of the forceps. The housing may also include one or more printed circuit boards and associated controls, one or more monopolar electrodes, one or more bipolar electrodes, one or more shields, one or more channels, or a combination thereof.

The connectivity systems described herein provide sufficient power and energy for combination electrosurgical devices. While industry standard electrosurgical generators typically provide sufficient power for only stand-alone monopolar or stand-alone bipolar electrosurgical devices, the connectivity systems described herein allow for sufficient power supply to a combination device via industry standard electrosurgical generator outlets. While such energy may traditionally be provided via a dedicated outlet, the systems herein allow for necessary energy provision via the stand-alone monopolar and bipolar outlets.

FIG. 1 shows example outlets for stand-alone monopolar and stand-alone bipolar outlets on an industry standard electrosurgical generator. The monopolar outlet 10 includes an HF output 12, a cut switch 14 and a coag switch 18. The bipolar outlet 18 includes two HF outputs 20, 22 and a coag switch 24.

Figure 2:
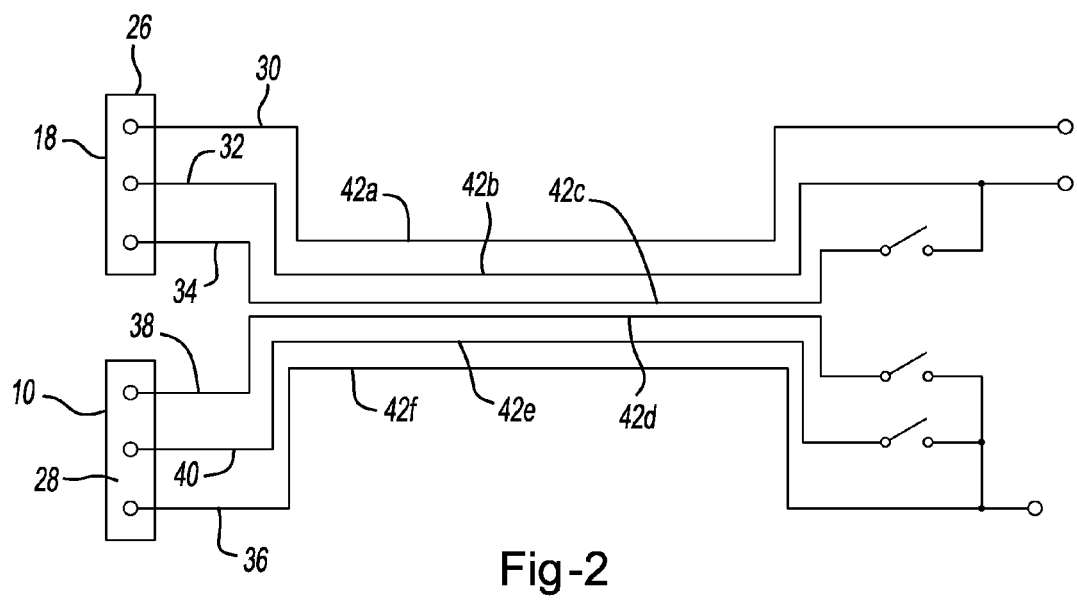
FIG. 2 shows an illustrative example of an industry standard monopolar and bipolar generator outlet arrangement connected to a combination monopolar/bipolar device.

FIG. 2 is a diagram depicting a connectivity system including a bipolar plug (e.g., bipolar connector) 26 and a monopolar plug (e.g. monopolar connector) 28. The bipolar plug 26 includes a plurality of conductors including a first bipolar HF lead 30 and a second bipolar HF lead 32. The bipolar plug further includes a bipolar coag switch return lead 34. The monopolar plug 28 includes a plurality of conductors including a monopolar HF lead 36 and a first and second monopolar switch return lead 38, 40. The first monopolar switch return lead 38 is a monopolar cut switch return lead and the second monopolar switch return lead 40 is a monopolar coag switch return lead. The diagram depicts no common lines, so that there are six lines 42a, 42b, 42c, 42d, 42e, 42f that form the cable running from the monopolar outlet 10 and bipolar outlet 18 to the electrosurgical device (not shown). The system further includes a bipolar activation switch 48, and two monopolar activation switches 50, 52. The monopolar switches include a monopolar cut activation switch 50 and a monopolar coag activation switch 52.

Figure 3:
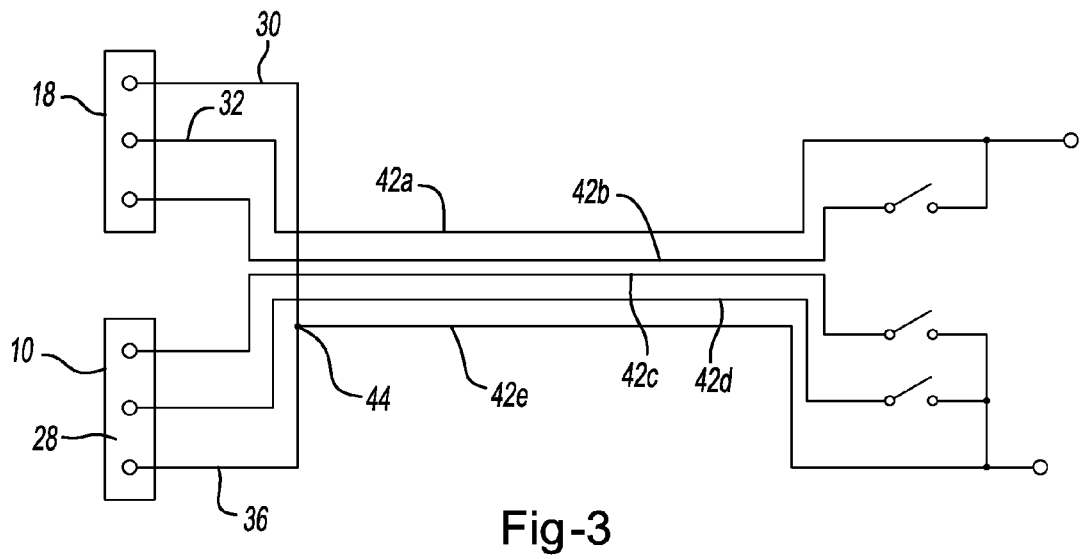
FIG. 3 shows an additional illustrative example of an industry standard monopolar and bipolar generator outlet arrangement connected to a combination monopolar/bipolar device.

FIG. 3 shows a connectivity system whereby the first bipolar HF lead 30 is common with the monopolar HF lead 36. Thus the common HF leads 30, 36 are connected (e.g., shunted) at a connection point 44 prior to connecting to the electrosurgical device itself (not shown). As a result of the common line, there are five lines 42a, 42b, 42c, 42d, 42e that form the cable running from the monopolar outlet 10 and bipolar outlet 18 to the electrosurgical device. The system further includes a first electrode 54 and a second electrode 56 within the electrosurgical device. FIG. 3 depicts that the second electrode 56 operates as both a monopolar electrode and bipolar electrode, as shown by the illustrated connectivity.

Figure 4:
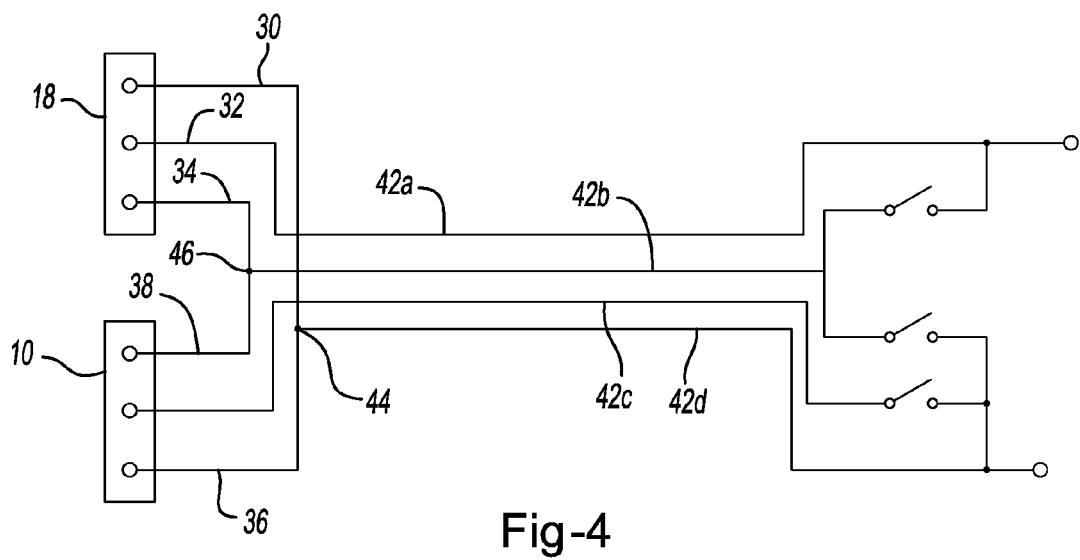
FIG. 4 shows an additional illustrative example of an industry standard monopolar and bipolar generator outlet arrangement connected to a combination monopolar/bipolar device.

FIG. 4 shows a connectivity system whereby the first bipolar HF lead 30 is common with the monopolar HF lead 36, as shown in FIG. 3, and also the bipolar switch return lead 34 is common with the first monopolar switch return lead 38 (e.g., the monopolar cut switch return lead). Thus, the common HF leads 30, 36 are connected (e.g., shunted) at a connection point 44 prior to connecting to the electrosurgical device itself not shown). Also, the common switch return leads 34, 38 are connected (e.g., shunted) at a connection point 46 prior to connecting with the electrosurgical device. As a result of the common line, there are four lines 42a, 42b, 42c, 42d that form the cable running from the monopolar outlet 10 and bipolar outlet 18 to the electrosurgical device. The system further includes a first electrode 54 and a second electrode 56 within the electrosurgical device. FIG. 4 depicts that the second electrode 56 operates as both a monopolar electrode and bipolar electrode, as shown by the illustrated connectivity.

Figure 5:
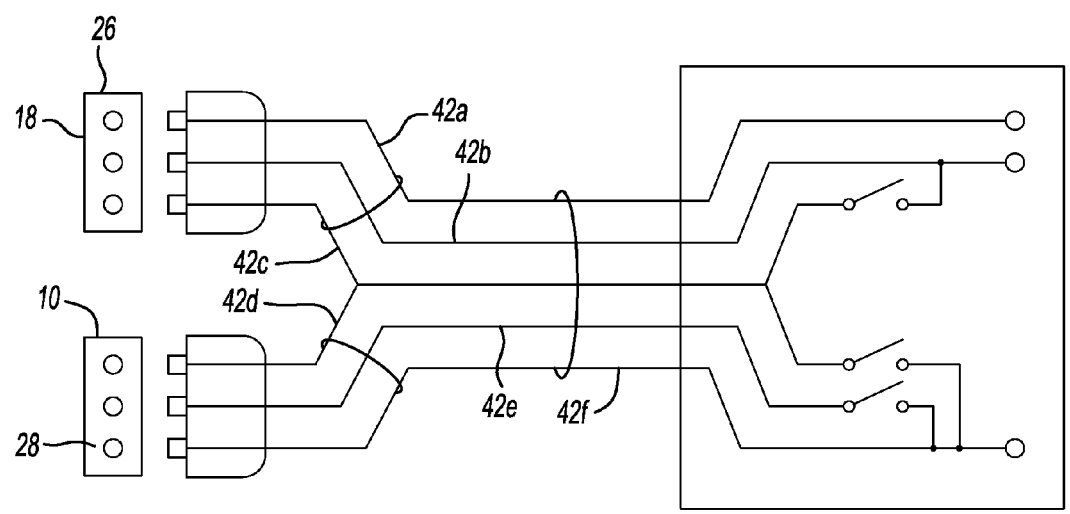
FIG. 5 shows an additional illustrative example of an industry standard monopolar and bipolar generator outlet arrangement connected to a combination monopolar/bipolar device.

FIG. 5 shows a connectivity system including a monopolar outlet 10 and bipolar outlet 18 prior to connection with the bipolar plug 26 and monopolar plug 28. The bipolar switch return lead 34 is common with the first monopolar switch return lead 38. The common switch return leads 34, 38 are connected (e.g., shunted) at a connection point 44 prior to connecting to the electrosurgical device itself (not shown). In addition, there are five lines 42a, 42b, 42c, 42d, 42e that form the cable running from the bipolar plug 26 and monopolar plug 28 to the electrosurgical device. The portions within the electrosurgical device 60 are indicated by the boxed area of the figure. The system further includes a first electrode 54, a second electrode 56, and a third electrode 58 within the electrosurgical device. FIG. 5 also depicts a bipolar activation switch 48, a monopolar cut activation switch 50 and a monopolar coag activation switch 52.

Figure 6:
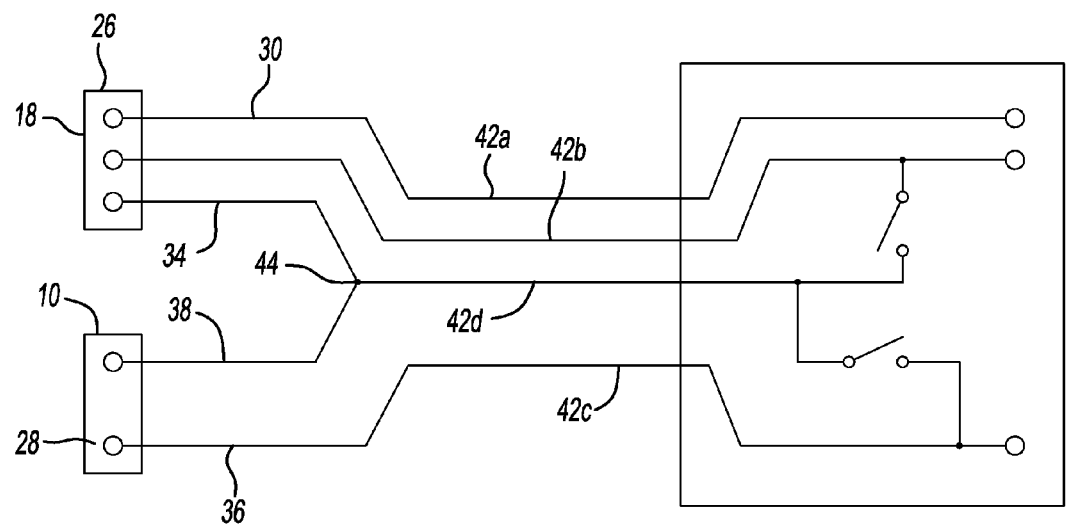
FIG. 6 shows an additional illustrative example of an industry standard monopolar and bipolar generator outlet arrangement connected to a combination monopolar/bipolar device.

FIG. 6 shows a connectivity system whereby the bipolar switch return lead 34 is common with the first (and only) monopolar switch return lead 38. The common switch return leads 34, 38 are connected (e.g., shunted) at a connection point 44 prior to connecting to the electrosurgical device itself (not shown). In addition, there are four lines 42a, 42b, 42c, 42d (given that there was only one monopolar switch lead as opposed to two) that form the cable running from the bipolar plug 26 and monopolar plug 28 to the electrosurgical device. The system further includes a first electrode 54, a second electrode 56, and a third electrode 58 within the electrosurgical device. FIG. 6 also depicts a bipolar activation switch 48, and a monopolar activation switch 50.

Figure 7:
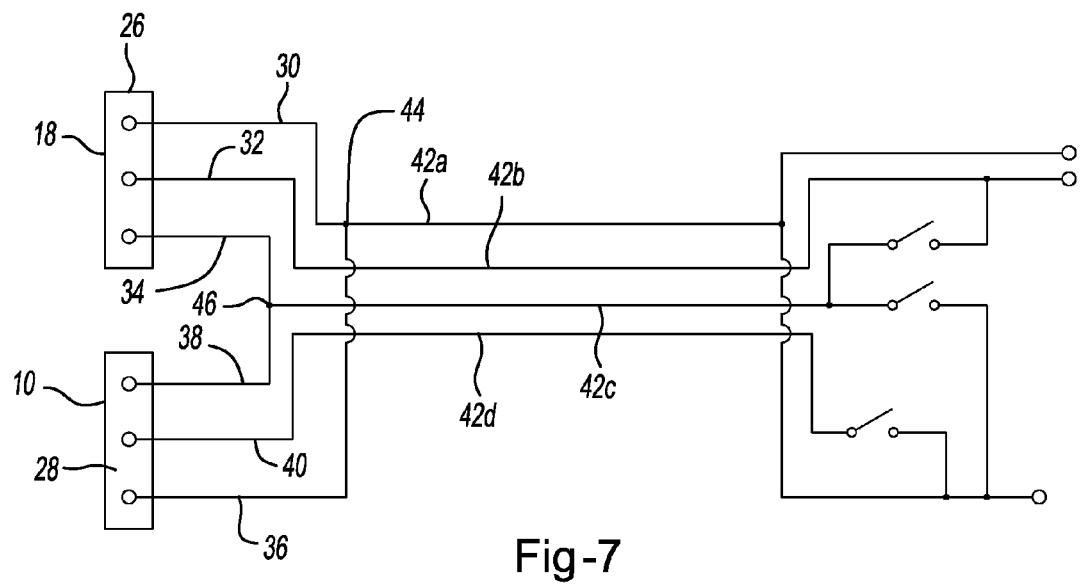
FIG. 7 shows an additional illustrative example of an industry standard monopolar and bipolar generator outlet arrangement connected to a combination monopolar/bipolar device.

FIG. 7 shows a connectivity system whereby the first bipolar HF lead 30 is common with the monopolar HF lead 36. Thus the common HF leads 30, 36 are connected (e.g., shunted) at a connection point 44 prior to connecting to the electrosurgical device itself (not shown). The bipolar switch return lead 34 is also common with the first monopolar switch return lead 38. The common switch return leads 34, 38 are connected (e.g., shunted) at a connection point 46 prior to connecting to the electrosurgical device itself (not shown). As a result, there are only four lines 42a, 42b, 42c, 42d that form the cable running from the bipolar plug 26 and monopolar plug 28 to the electrosurgical device. The four lines connect to a first electrode 54, a second electrode 56, and a third electrode 58 within the electrosurgical device.

FIG. 7 also depicts a bipolar activation switch 48, and a monopolar activation switch 50.

Figure 8:
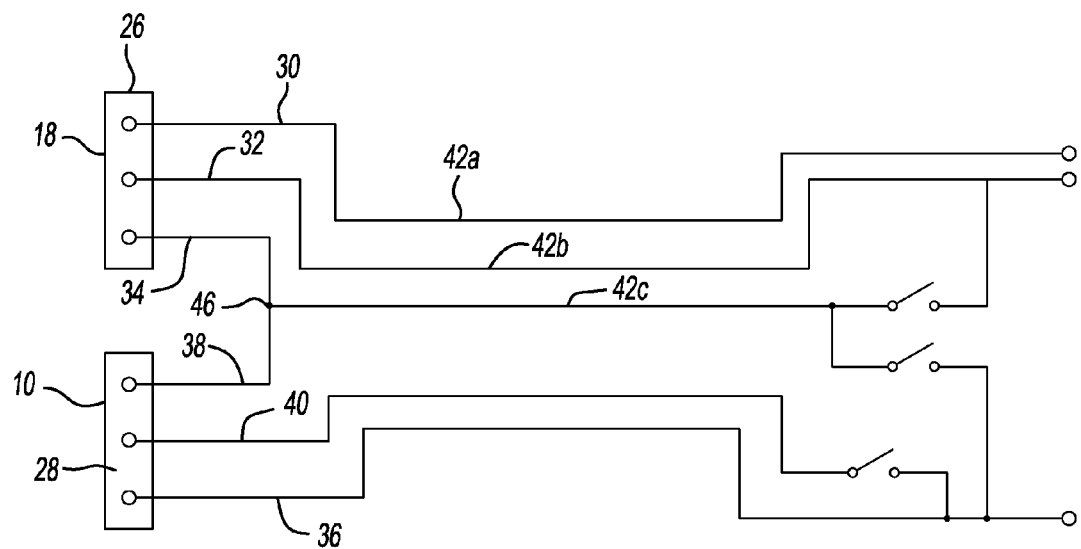
FIG. 8 shows an additional illustrative example of an industry standard monopolar and bipolar generator outlet arrangement connected to a combination monopolar/bipolar device.

FIG. 8 shows a connectivity system whereby the bipolar switch return lead 34 is common with the first monopolar switch return lead 38. The common switch return leads 34, 38 are connected (e.g., shunted) at a connection point 44 prior to connecting to the electrosurgical device itself (not shown). In addition, there are five lines 42a, 42b, 42c, 42d, 42e that form the cable running from the bipolar plug 26 and monopolar plug 28 to the electrosurgical device.

Figure 9:
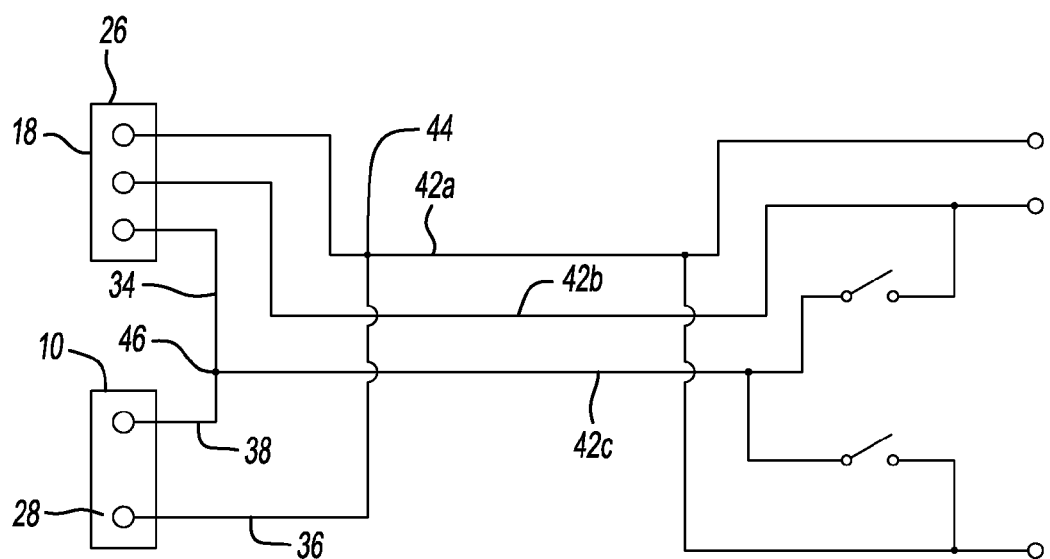
FIG. 9 shows an additional illustrative example of an industry standard monopolar and bipolar generator outlet arrangement connected to a combination monopolar/bipolar device.

FIG. 9 shows a connectivity system whereby the first bipolar HF lead 30 is common with the monopolar HF lead 36. Thus the common HF leads 30, 36 are connected (e.g., shunted) at a connection point 44 prior to connecting to the electrosurgical device itself (not shown). The bipolar switch return lead 34 is common with the first (and only) monopolar switch return lead 38. The common switch return leads 34, 38 are connected (e.g., shunted) at a connection point 46 prior to connecting to the electrosurgical device itself (not shown). In addition, there are three lines 42a, 42b, 42c (given that there was only one monopolar switch lead as opposed to two) that form the cable running from the bipolar plug 26 and monopolar plug 28 to the electrosurgical device.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An electrical cable comprising:
    a first plug, including a first, second and third conductor extending therefrom, wherein the first and second conductors are first and second electrosurgical leads and the third conductor is a first electrosurgical activation switch return lead;
    a first electrosurgical activation switch connected between one of the electrosurgical leads and the first electrosurgical activation switch return lead;
    a second plug adapted to plug including a fourth, fifth and a sixth conductor extending therefrom, wherein the fourth conductor is a third electrosurgical lead and the fifth and sixth conductors are second and third electrosurgical activation switch return leads;
    a second electrosurgical activation switch connected between the fourth conductor and the fifth conductor;
    a third electrosurgical activation switch connected between the fourth conductor and the sixth conductor;
    wherein the third conductor is a shared conductivity line integrated with one of the fifth or sixth conductors.

2. The cable of claim 1, wherein at least one of the switch return leads is a monopolar cut switch return lead or a monopolar coag return lead.

3. The cable of claim 2, wherein at least one of the switch return leads is a bipolar switch return lead.

4. The cable of claim 1, wherein the cable includes exactly six conductors.

5. The cable of claim 1, wherein the fourth conductor is a shared conductivity line integrated with either the first or second conductor.

6. The cable of claim 1 wherein:
    (i) the first plug engages a bipolar outlet;
    (ii) the second plug engages a monopolar outlet;
    (iii) the first electrosurgical activation switch is a bipolar activation switch; and
    (iv) the second and third electrosurgical activation switches are monopolar activation switches.

7. The cable of claim 6, wherein the fifth conductor is a monopolar cut switch return lead.

8. The cable of claim 6, wherein the sixth conductor is a monopolar coag switch return lead.

9. The cable of claim 6, wherein the third conductor is a shared conductivity line integrated with the fifth conductor.

10. The cable of claim 6, wherein the third conductor is a shared conductivity line integrated with the sixth conductor.

11. The cable of claim 1, wherein at least one conductor is a monopolar HF lead and at least one conductor is a bipolar HF leads.

12. An electrical cable comprising:
    a first plug configured to plug into a bipolar outlet, the first plug including a first, second and third bipolar conductor extending therefrom, wherein the first and second bipolar conductors are bipolar HF leads and the third bipolar conductor is a bipolar switch return lead,
    a bipolar activation switch connected between one of the bipolar HF leads and the bipolar switch return lead;
    a second plug adapted to plug into a monopolar outlet, the second plug including a first, second and third monopolar conductor extending therefrom, wherein the first monopolar conductor is a monopolar HF lead and the second and third monopolar conductors are monopolar switch return leads;
    a monopolar cut activation switch connected between the monopolar HF lead and the second monopolar switch return lead;
    a monopolar coag activation switch connected between the monopolar HF lead and the third monopolar switch return lead;
    wherein the bipolar switch return lead is a shared conductivity line integrated with one of the second or third monopolar switch return leads.

* * * * *